(12) United States Patent
Graffam et al.

(10) Patent No.: US 8,496,644 B2
(45) Date of Patent: Jul. 30, 2013

(54) DRAINAGE CATHETER TIP SHAPE CONFIGURATION

(75) Inventors: Richard Graffam, Marlborough, MA (US); Ben Morris, Jeffersonville, IN (US); Chuck Bourgeois, Wilmington, MA (US)

(73) Assignee: AngioDynamics, Inc., Latham, NY (US)

( * ) Notice: Subject to any disclaimer, the term of this patent is extended or adjusted under 35 U.S.C. 154(b) by 749 days.

(21) Appl. No.: 12/641,265

(22) Filed: Dec. 17, 2009

(65) Prior Publication Data

US 2011/0152842 A1    Jun. 23, 2011

(51) Int. Cl.
*A61M 1/00* (2006.01)

(52) U.S. Cl.
USPC .......................................... 604/540; 604/530

(58) Field of Classification Search
USPC ......... 604/19, 95.04, 317, 540, 530; 600/149; 264/519
See application file for complete search history.

(56) References Cited

U.S. PATENT DOCUMENTS

| | | | |
|---|---|---|---|
| 5,419,764 A | 5/1995 | Roll | |
| 5,472,435 A | 12/1995 | Sutton | |
| 5,489,270 A * | 2/1996 | van Erp | 604/95.04 |
| 5,941,849 A | 8/1999 | Amos, Jr. et al. | |
| 6,042,577 A | 3/2000 | Chu et al. | |
| 6,159,177 A | 12/2000 | Amos, Jr. et al. | |
| 6,231,542 B1 | 5/2001 | Amos, Jr. et al. | |
| 6,315,789 B1 | 11/2001 | Cragg | |
| 6,547,761 B2 | 4/2003 | Liu | |
| 6,673,060 B1 | 1/2004 | Fleming, III | |
| 6,893,418 B2 | 5/2005 | Liu | |
| 7,351,222 B2 | 4/2008 | Sauvageau | |

* cited by examiner

*Primary Examiner* — Tatyana Zalukaeva
*Assistant Examiner* — Benedict L Hanrahan
(74) *Attorney, Agent, or Firm* — Peter J. Flora

(57) ABSTRACT

A percutaneous catheter includes a longitudinal catheter shaft having a distal end, a proximal end, a hollow portion, and a wall portion, a wire embedded within said wall portion at said distal end wherein said wire forms a pigtail curve when in a relaxed state, and a stylet capable of entering said hollow portion of said longitudinal catheter at said proximal end wherein said stylet substantially straightens said longitudinal catheter at said distal end.

4 Claims, 4 Drawing Sheets

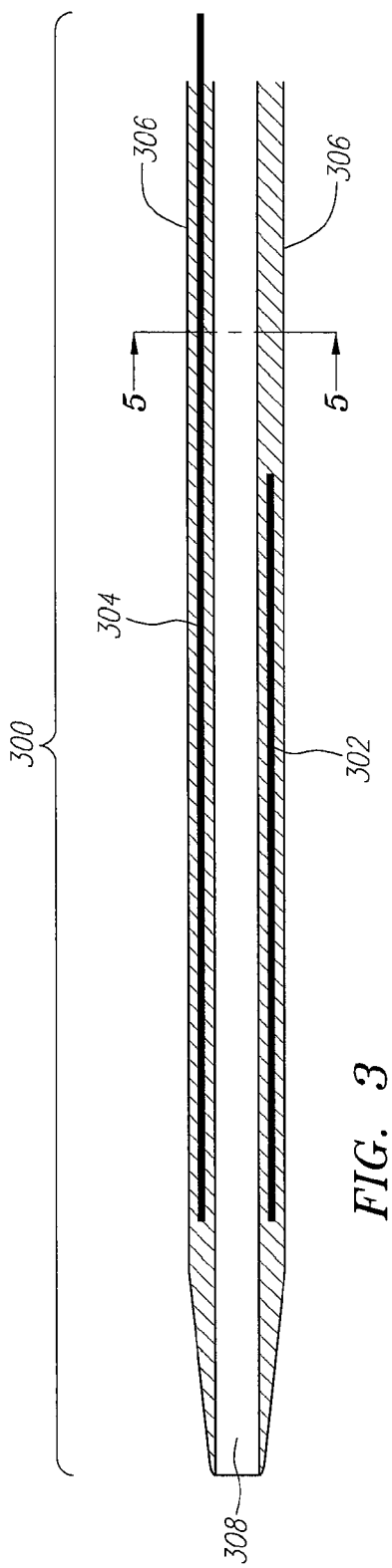
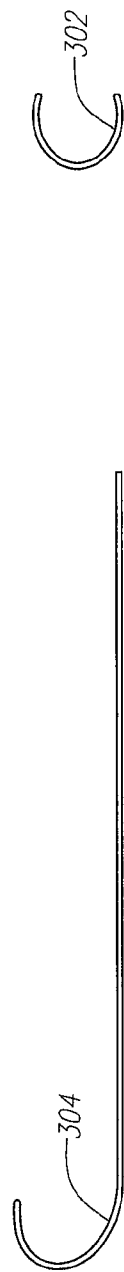
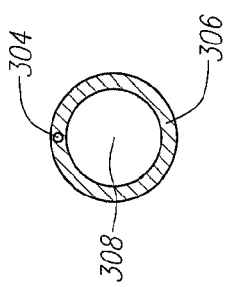
FIG. 3
FIG. 4A
FIG. 4B
FIG. 5

DRAINAGE CATHETER TIP SHAPE CONFIGURATION

FIELD

The present invention relates generally to indwelling drainage catheters, and more particularly, to a catheter tip that is configured to naturally form a pigtail curve upon manipulation of a stylet or a control wire, which allows the catheter to be introduced and locked into a body cavity.

BACKGROUND

Flexible catheters are used for percutaneous drainage of an abscess or pocket of fluid in the body to the exterior by means of gravity or negative pressure. Fluid collection may be the result of an infection, surgery, trauma or other causes. Typical fluids include biliary, nephrostomy, pleural, urinary, and mediastinal collections. As an alternative to providing drainage, these catheters can also be used to introduce substances, such as fluids, into a patient's body.

In percutaneous drainage procedures, a catheter is typically introduced into a patient through a hypodermic needle or a trocar. A guidewire is inserted through the needle, which is then removed. The catheter tube, with a stiffening cannula, then passes over the previously emplaced guide wire into the drainage site in the body cavity. The stiffening cannula is then removed.

Once a drainage catheter is in position in the body cavity, it is desirable to anchor the catheter before drainage begins. Typically, this can be done by forming a restraining portion in the distal end of the catheter in the form of a pigtail or "J-curve." For a pigtail configuration, a flexible tension member, such as a suture thread, extends through draw ports at two spaced positions along the distal portion of the catheter. The restraining portion is conventionally activated by manually pulling the suture thread so that the two draw ports move toward each other as the pigtail loop forms at the distal end of the catheter. When the suture thread is taut, it prevents the pigtail loop from straightening by holding the juxtaposed portions of the catheter together in a locked position. The restraining portion is thus in a shape capable of resisting displacement from the body cavity. Once actuated, this restraining portion prevents removal of the catheter. When the catheter is ready to be removed, the cannula is inserted through the lumen until it reaches the pigtail loop. The restraining portion at the distal end is unlocked by cutting or releasing the suture at the proximal end, where the catheter protrudes from the body.

A preformed curve in the shape of a malecot rib has also been used as a possible anchoring mechanism. In this configuration, longitudinal slits are located in the restraining portion of the catheter at the distal end. The rib is activated in a similar manner as the pigtail configuration by manipulating a tension member, except the restraining portion is formed in the shape of multiple wings (typically two or four) instead of a pigtail.

Successful procedures involving percutaneous drainage depend upon the initial placement of the drainage catheter and having the catheter remain in place for the duration of the treatment. Without adequate anchoring or support, catheter dislodgment may result due to body movements by the patient or under other conditions.

Described herein are unique devices, systems and methods for supplementing the pigtail or malecot anchoring mechanism by using a catheter that is configured to naturally form a pigtail curve upon manipulation of a stylet or a control wire.

SUMMARY

The devices, systems and methods described herein relate to percutaneous drainage catheters and an anchoring structure or mechanism for indwelling catheters (both short and long-term). This feature allows for the catheter to be introduced or locked into the anatomy via stabilized formation of a pigtail structure at the drainage catheter tip.

In one embodiment, the catheter includes a longitudinal catheter shaft having a distal end, a proximal end, a hollow portion, and a wall portion, a wire embedded within said wall portion at said distal end wherein said wire forms a pigtail curve when in a relaxed state, and a stylet capable of entering said hollow portion of said longitudinal catheter at said proximal end wherein said stylet substantially straightens said longitudinal catheter at said distal end.

In another embodiment, the catheter includes a longitudinal catheter shaft having a distal end, a proximal end, a hollow portion, and a wall portion, a first wire embedded within said wall portion at said distal end wherein said first wire forms a C-curve when in a relaxed state, a second wire embedded opposite to said first wire within said wall portion wherein said second wire forms at least a C-curve portion and straight portion when in a relaxed state, and wherein said straight portion of said second wire is exposed at said proximal end of said longitudinal catheter shaft.

A method of affixing a catheter within a body cavity includes inserting a distal end of a catheter into the body cavity, the catheter including a longitudinal catheter shaft having a distal end, a proximal end, a hollow portion, and a wall portion, a wire embedded within said wall portion at said distal end wherein said wire forms a pigtail curve when in a relaxed state, and a stylet capable of entering said hollow portion of said longitudinal catheter at said proximal end wherein said stylet substantially straightens said longitudinal catheter at said distal end, and securing the catheter within the body cavity by removing said stylet from said hollow portion of said longitudinal catheter.

Yet another method of affixing a catheter within a body cavity includes inserting distal end of a catheter into the body cavity, the catheter including a longitudinal catheter shaft having a distal end, a proximal end, a hollow portion, and a wall portion, a first wire embedded within said wall portion at said distal end wherein said first wire forms a C-curve when in a relaxed state, a second wire embedded opposite to said first wire within said wall portion wherein said second wire forms a C-curve at a first portion and is substantially straight at a second portion when in a relaxed state, and wherein said second portion of said second wire is exposed at said proximal end of said longitudinal catheter shaft, and securing the catheter within the body cavity by twisting said second portion of said second wire so as to allow said first and second wires to form a pigtail curve.

Of the various features described, the structures herein offer a number of advantages in their construction and ability to anchor the drainage catheter in various applications. Other systems, methods, features and advantages will be or will become apparent to one of ordinary skill in the art upon examination of the following figures and detailed description. It is intended that all such additional systems, methods, features and advantages be included within this description, be within the scope of the devices, systems and methods described herein, and be protected by the accompanying claims.

BRIEF DESCRIPTIONS OF THE DRAWINGS

The figures provided herein are not necessarily drawn to scale, with some components and features being exaggerated for clarity. Each of the figures diagrammatically illustrates aspects of the embodiments.

FIG. 3 is a cross sectional view of a straightened drainage catheter tip with a two-wire feature.

FIGS. 4a and 4b are perspective views depicting exemplary structures of the individual wires used in a drainage catheter tip with a two-wire feature.

FIG. 5 is a cross sectional view of a straightened drainage catheter tip with a two-wire feature.

DETAILED DESCRIPTION

The devices, systems and methods described herein can be used for introducing a percutaneous catheter into a patient and anchoring the catheter into the body of the patient to facilitate draining fluid or removing other materials from the body. Alternatively, the catheter can introduce substances, such as fluids, into the patient's body.

Figure 1A:
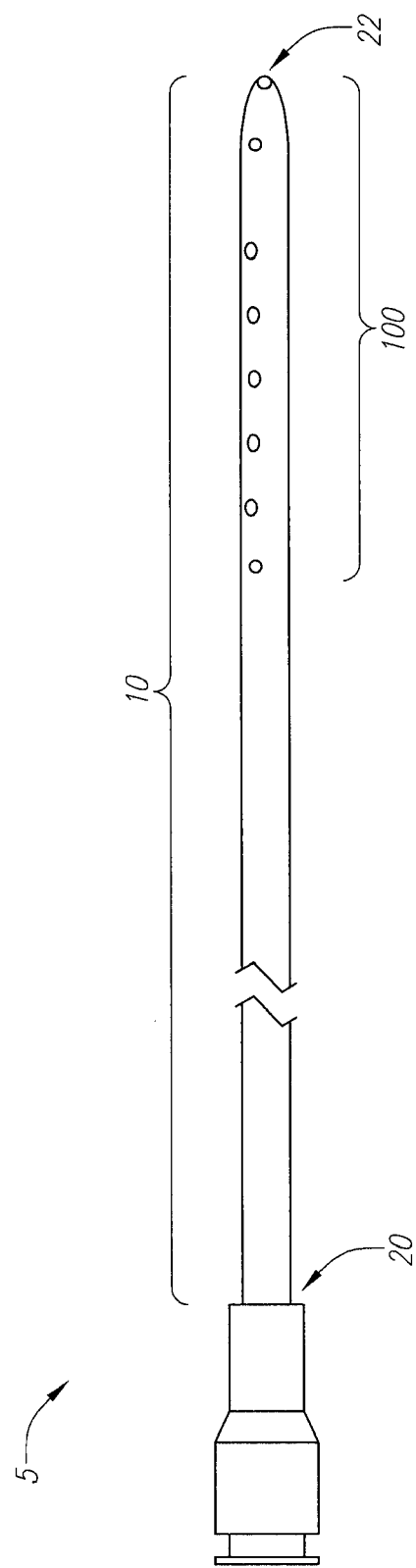
FIG. 1a is a perspective view of a drainage catheter shown prior to activation of the "pigtail" loop formation.

Referring to FIG. 1a, a perspective view of a drainage catheter prior to activation of the "pigtail" loop formation is shown. FIG. 1A depicts a catheter 5 comprising a flexible, elongate tube member 10 having a proximal end 20, a distal end 22, and a catheter tip 100. The elongate tube member 10 defines an internal lumen, which extends through the catheter 5. When the catheter 5 is first introduced into the patient, a cannula can be inserted into the catheter lumen to help straighten the catheter 5. Typically, when employing the catheter 5 into a body cavity, the catheter 5 has a diameter of between 6 and 18 French (Fr).

Figure 1B:
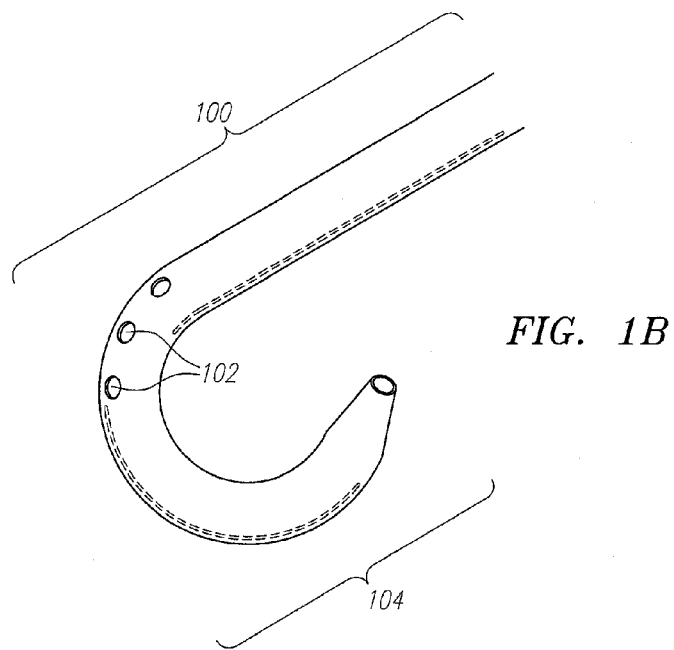
FIG. 1b is a perspective view of a drainage catheter tip in a "pigtail" loop configuration as an anchoring mechanism, shown with stylet removed.

FIG. 1b is a perspective view of a drainage catheter tip 100 in a "pigtail" loop 104 configuration as an anchoring mechanism, shown with stylet removed. FIG. 1b depicts the distal portion of a catheter 5 comprising a flexible, elongate tube member 10 and a restraining portion, the restraining portion comprising the pigtail loop 104. The wall of the drainage catheter tip 100 toward the distal end includes a series of drainage holes, or perforations 102. The pigtail loop 104 maintains its "pigtail" formation by an embedded, preformed shape memory material (See FIG. 2). When the catheter 5 is first introduced into the patient (not shown), a cannula, stylet, or other rigid straightening device may be inserted into the catheter lumen to help straighten the catheter 5 and facilitate insertion. When the catheter drainage tip 100 reaches the drainage site, the stylet is withdrawn proximally, and the draw ports 102 are drawn closer together in the pigtail configuration. As a result, the pigtail loop 104 configuration is formed, as shown in FIG. 1b.

Figure 2:
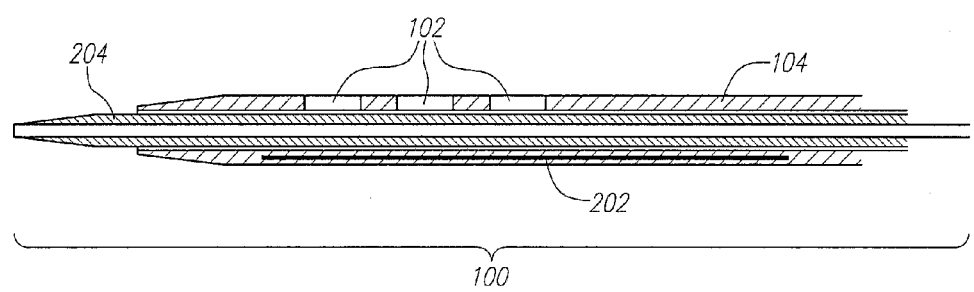
FIG. 2 is a cross sectional view of a straightened drainage catheter tip, shown with stylet inserted.

Referring to FIG. 2, a cross sectional view of a straightened drainage catheter tip 100, depicted with stylet 204 inserted in the lumen, is shown. Here, the pigtail loop 104 portion of the distal end of the catheter 5 has been substantially straightened by insertion of a stylet 204. For purposes of this disclosure, one of ordinary skill in the art may appreciate that a cannula or any other straightening apparatus may likewise be used to substantially perform the same objective. As herein depicted, the shape memory material 202, which forms a C-curve in its relaxed state (FIG. 4b), may consist of any material capable of being temporarily manipulated and deformed in infinite ways without affecting its ability to return to its pre-shaped relaxed state, in this instance, a C-curve. It is well known in the field that Nickel Titanium alloy (hereinafter Nitinol) has properties that are conducive to its application in medical devices since this alloy exhibits two closely related and very unique properties, namely, shape memory and superelasticity. As alluded to above, superelasticity occurs at a narrow temperature range just above its transformation temperature; in this case, no heating is necessary to cause the undeformed shape to recover, exhibiting enormous elasticity in the order of 10-30 times that of ordinary metal. The shape memory material 202 may be of some finite length that substantially extends the length of the pigtail 104 region of the catheter tip 100.

The pigtail anchoring region 104 can have one or more series of perforations 102 that start and stop on different locations along the catheter tip 100. The pitch, or the distance from one point on the perforation 102 to a corresponding point on an adjacent perforation 102 measured parallel to the axis of the catheter tip 100, may vary. For example, the perforations 102 may be spaced closer together at the proximal end, and farther apart at the distal end of the pigtail 104 portion, or vice versa. This configuration may facilitate the interfacing of the perforations 102 with different types of tissue encountered at various parts of the catheter. Additionally, the angles of the perforations 102 relative to the longitudinal axis of the catheter 5 may also vary. The perforations 102 themselves may vary in cross-sectional geometry (i.e., semi-circular, triangular, trapezoid) and be placed at one or more discrete locations along the catheter shaft 10. For sake of clarity and simplicity, FIGS. 1 and 2 depict circular perforations configured normal to the catheter's 5 longitudinal axis.

The catheter 100 may be constructed of thermoplastic polymer such as polyurethane, ethyl vinyl acetate (EVA), polyether block amide elastomer, polypropylene, or polyolefin elastomers. The catheter system can also be constructed of a thermoset plastic like silicone. The pigtail anchoring region 104 may likewise be flexible but may be constructed of a different material than the remainder of the catheter shaft 100.

Referring to FIG. 3, another exemplary embodiment of a straightened drainage catheter tip with a two-wire feature is shown. This embodiment includes two embedded wires 302, 304 within the wall 306 of the catheter 300—with one wire 304 extending substantially further along the longitudinal axis than the other wire 302 so that the exposed wire 304 may be manually manipulated to revert to its relaxed state and back to its tensioned state. Unlike the embodiment previously described in relation to FIGS. 1 and 2, this exemplary embodiment does not rely on a cannula or stylet for straightening of the catheter 300. Rather, the two-wire feature facilitates transitioning between a pigtail and straightened configuration solely by applying torsional force to the exposed wire 304. As such, the remainder of the catheter's 300 configuration with respect to the perforations 102 and the basic overall structure, i.e., a catheter wall 306 circumferentially enveloping a lumen portion 308 remains identical to the first embodiment described.

Further, FIGS. 4a and 4b are perspective views depicting exemplary structures of the individual wires 302, 304 used in a drainage catheter tip 300 with a two-wire feature. Again, one of ordinary skill in the art may appreciate that the wires 302, 304 may consist of Nitinol for the very same reasons previously stated. Moreover, although the wires 302, 304 depicted within FIG. 4 substantially comprise a C-curve, one may adopt different shaped material, e.g. a circle, without straying from the express teachings of this disclosure.

Referring to FIG. 5, a cross sectional view (A-A) of a straightened drainage catheter tip 300 with a two-wire feature is shown. As depicted, at cross section A-A, only one wire 304 embedded within the catheter wall 306. The wire 304 is the wire that is exposed for external torsional manipulation. The catheter's lumen portion 308, however, remains completely unobstructed and remains aptly able to perform its drainage objective.

Figure 6A:
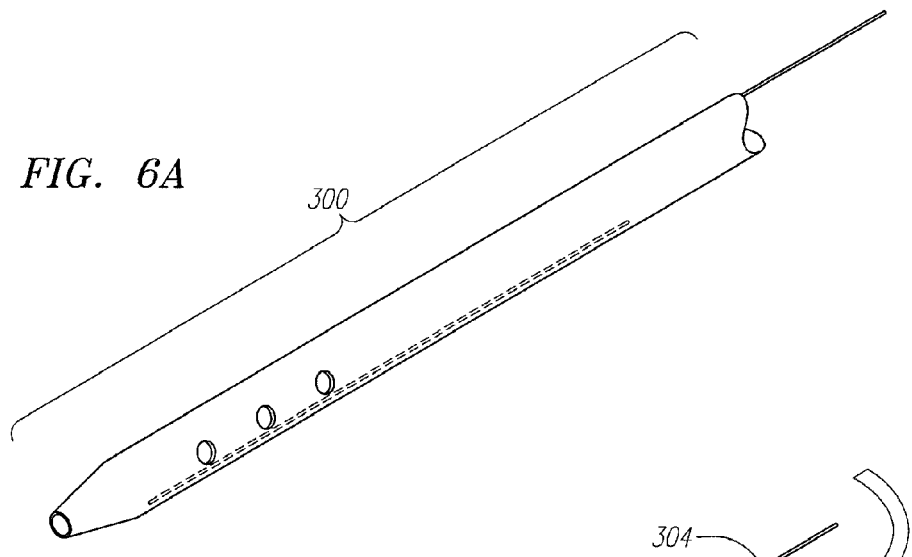
FIGS. 6a and 6b are perspective views of a drainage catheter tip with a two-wire feature in a straightened and a "pigtail" loop configuration, respectively.
Figure 6B:
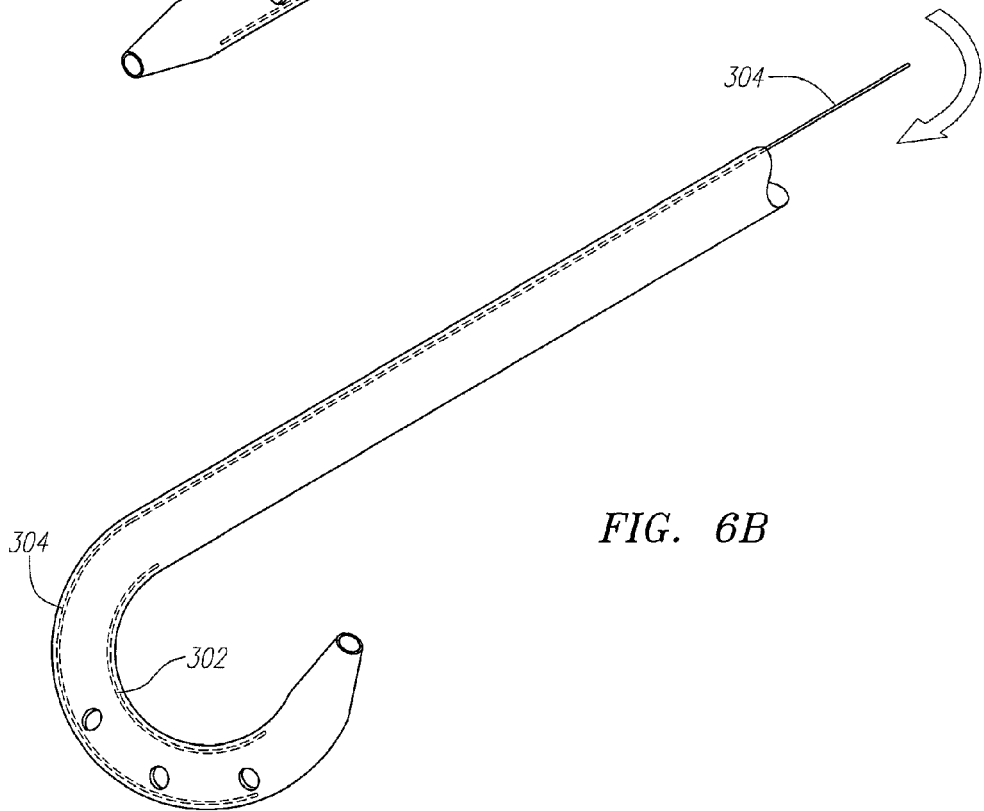

Referring to FIGS. 6a and 6b, the alternative embodiment is shown in a straightened and a "pigtail" loop configuration, respectively. Similar to the first described embodiment, FIG. 6b depicts the substantially similar pigtail structure as shown in FIG. 1b—thus, the identical objectives are equally met. From a tensioned state, manual torsional force may be applied to wire 304. Due to the shaped materials relaxed state, the catheter 300 may tend to shift to form a pigtail loop with very little applied force. While in a relaxed state, wire 302 may form the inner portion of the pigtail loop, while the longer wire 304 may form the outer portion of same.

The anchoring regions mentioned in the foregoing discussion and shown above in FIGS. 1b and 6b may replace or supplement the traditional anchoring mechanism embodied by a traditional pigtail loop shape or other shapes in the restraining portion of the catheter tip 100, 300. Although not shown in the figures, the restraining portion of the catheter may vary as follows. The restraining portion as referenced herein may span one or more sections along the catheter that defines a traditional anchoring mechanism (embodied by the pigtail loop configuration or the malecot rib configuration). The length of the restraining portion may vary, according to the desired application. Typically, the restraining portion is located in the region medial to distal on the catheter, where the anchoring mechanism is to be activated in the body cavity. However, it is contemplated that the restraining portion can also be positioned closer to the proximal end of the catheter, as well as at multiple locations at any point between the proximal end and the distal end. In an exemplary embodiment, in addition to a first restraining portion comprising a pigtail configuration positioned near the distal end of the catheter, a second restraining portion comprising one or more anchoring geometries can be strategically positioned along the catheter between the proximal end and the first restraining portion, such that anchoring occurs at a tissue interface area in the body (e.g., at the skin of the patient).

Also contemplated herein are methods that can be performed using the subject devices or by other means. The methods can all comprise the act of providing a suitable device. Such provision can be performed by the end user. In other words, the "providing" merely requires the end user obtain, access, approach, position, set-up, activate, power-up or otherwise act to provide the requisite device in the subject method. Methods recited herein can be carried out in any order of the recited events which is logically possible, as well as in the recited order of events.

Exemplary embodiments, together with details regarding material selection and manufacture have been set forth above. As for other details of the presently described subject matter, these can be appreciated in connection with the above-referenced patents and publications as well as generally know or appreciated by those with skill in the art. The same can hold true with respect to method-based aspects in terms of additional acts as commonly or logically employed.

In addition, though the devices, systems and methods described herein have been presented herein in reference to exemplary embodiments, optionally incorporating various features, the devices, systems and methods described herein are not to be limited to that which is described or indicated as contemplated with respect to each variation. Various changes can be made to the subject matter described herein, and equivalents (whether recited herein or not included for the sake of some brevity) can be substituted without departing from the true spirit and scope of the disclosure.

Also, it is contemplated that any optional feature of the inventive variations described can be set forth and claimed independently, or in combination with any one or more of the features described herein. Stated otherwise, it is to be understood that each of the improvements described herein independently offer a valuable contributions to the state of the art. So too do the various other possible combination of the improvements/features described herein and/or incorporated by reference, any of which can be claimed.

Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Likewise, use of the term "typically" does not exclude other possibilities. It can indicate a preference, however, for the stated characteristic. Except as specifically defined herein, all technical and scientific terms used herein are to be given as broad a commonly understood meaning as possible while maintaining claim validity.

The invention claimed is:

1. A method of fixing a catheter within a body cavity comprising:
    inserting a distal end of a catheter into a body cavity, the catheter including a longitudinal catheter shaft having a distal end, a proximal end, a hollow portion, and a wall portion, a first wire embedded within said wall portion at said distal end wherein said first wire forms a C-curve when in a relaxed state, a second wire embedded opposite to said first wire within said wall portion;
    wherein said second wire forms a C-curve at a first portion, is substantially straight at a second portion of said second wire, and is exposed at said proximal end of said longitudinal catheter shaft;
    securing the catheter within the body cavity by twisting said second portion of said second wire so as to allow said first and second wires to form a pigtail curve; and
    wherein neither said first or second wires are withdrawn substantially backwards along the longitudinal catheter shaft while securing the catheter.

2. The method of fixing a catheter within a body cavity of claim 1, wherein the first and second wire is manufactured from a shape memory alloy.

3. The method of fixing a catheter within a body cavity of claim 2, wherein the shape memory alloy is Nitinol.

4. The method of fixing a catheter within a body cavity of claim 1, wherein the longitudinal catheter shaft has a plurality of perforations at said distal end.

* * * * *